(12) United States Patent
Umemura et al.

(10) Patent No.: US 7,316,989 B2
(45) Date of Patent: Jan. 8, 2008

(54) COMPOSITIONS INDUCING PLANTS DISEASE-RESISTANCE AND PROCESS FOR PRODUCING THE SAME

(75) Inventors: Kenji Umemura, Saitama-Ken (JP); Hideki Usami, Saitama-Ken (JP); Yoshihisa Tomoda, Saitama-Ken (JP); Shigeki Tanino, Kanagawa-Ken (JP)

(73) Assignee: Meiji Seika Kaisha, Ltd, Tokyo-To (JP)

( * ) Notice: Subject to any disclaimer, the term of this patent is extended or adjusted under 35 U.S.C. 154(b) by 0 days.

(21) Appl. No.: 10/488,137

(22) PCT Filed: Aug. 28, 2002

(86) PCT No.: PCT/JP02/08686

§ 371 (c)(1),
(2), (4) Date: Feb. 26, 2004

(87) PCT Pub. No.: WO03/020032

PCT Pub. Date: Mar. 13, 2003

(65) Prior Publication Data

US 2004/0198604 A1    Oct. 7, 2004

(30) Foreign Application Priority Data

Aug. 28, 2001  (JP) .............................. 2001-257800

(51) Int. Cl.
*A01N 25/32* (2006.01)
(52) U.S. Cl. ........................................ 504/111; 514/62
(58) Field of Classification Search ................ 504/117, 504/292, 116.1, 111; 514/62
See application file for complete search history.

(56) References Cited

U.S. PATENT DOCUMENTS

| 4,281,021 A | 7/1981 | Iizuka et al. | |
| 4,981,618 A * | 1/1991 | Bruneteau et al. | ............ 554/40 |

FOREIGN PATENT DOCUMENTS

| EP | 0 753 259 A2 | 1/1997 |
| EP | 0 832 557 A1 | 4/1998 |
| EP | 0 922 387 A1 | 6/1999 |
| JP | 56-44040 | 10/1981 |
| JP | 56-44040 B2 | 10/1981 |
| JP | 57-152883 | 9/1982 |
| JP | 5748087 B2 | 10/1982 |
| JP | 05-331016 | 12/1993 |
| JP | 9124411 | 5/1997 |
| JP | 11-029412 | 2/1999 |
| WO | 98/47364 A1 | 10/1998 |

OTHER PUBLICATIONS

M. Bostock, "Aerial Spraying of 2,4,5-T and Human Birth Malformations: An Epidemiological Investigation", Science, 1981, pp. 349-360, vol. 212, No. 17.

Jinichiro Koga et al., "Cerebrosides A and C, Sphingolipid Elicitors of Hypersensitive Cell Death and Phytoalexin Accumulation in Rice Plants", The Journal of Biological Chemistry, 1998, pp. 31985-31991, vol. 273, No. 48.

Genshiro Kawai et al., "Fruiting of Schizophyllum commune Induced by Certain Ceramides and Cerebrosides from *Penicillium funiculosum*", Agric. Biol. Chem., 1985, pp. 2137-2146, vol. 49, No. 7.

Genshiro Kawai, "Molecular species of cerebrosides in fruiting bodies of Lentinus edodes and their biological activity", Biochimica et Biophysica Acta, 1989, pp. 185-190, vol. 1001.

Janice K. Sharp et al., "The Primary Structures of One Elicitor-active and Seven Elicitor-inactive Hexa (β-D-glucopyranosyl)-D-glucitols Isolated from the Mycelial Walls of *Phytophthora megasperma* f. sp. Glycinea", The Journal of Biological Chemistry, 1984, pp. 11321-11336, vol. 259, No. 18.

Robert D. Sitrin et al., "Isolation and Structure Determination of Pachybasium Cerebrosides Which Potentiate the Antifungal Activity of Aculeacin", The Journal of Antibiotics, 1987, pp. 469-480, vol. XLI, No. 4.

Kenji Umemura et al., "Cerebroside Elicitors Found in Diverse Phytopathogenes Activate Defense Responses in Rice Plants", Plant Cell Physiol., 2000, pp. 676-683, vol. 41, No. 6.

Takeshi Yamaguchi et al., "Differences in the Recognition of Glucan Elicitor Signals between Rice and Soybean: β-Glucan Fragments from the Rice Blast Disease Fungus *Pyricularia oryzae* That Elicit Phytoalexin Biosynthesis in Suspension-Cultured Rice Cells", The Plant Cell, 2000, pp. 817-826, vol. 12.

Akiyoshi Sawabe, "Structural analyses of complex lipids from mushrooms by mass spectrometry", Symposium on the chemistry of Natural Products, Symposium Papers, 1996, pp. 373-378.

Yoshiyuki Mizushina, "A mushroom fruiting body-inducing substance inhibits activities of replicative DNA polymerases", Biochemical and Biophysical Research Communications, 1998, pp. 17-22, vol. 249, No. 1.

Steven B. Levery, "Comparative analysis of ceramide structural modification found in fungal cerebrosides by electrospray tandem mass spectrometry with low energy collision-induced dissociation of Li+ adductions, Rapid Communications in Mass Spectrometry", 2000, pp. 551-563, vol. 14, No. 7.

Genshiro Kawai, "Molecular species of cerebrosides in fruiting bodies of Lentinus edodes and their biological activity", Biochimica et Biophysica Acta, 1989, pp. 185-190, vol. 1001, No. 2.

Genshiro Kawai, "Fruiting of Schizophyllum commune induced by certain ceramides and cerebrosides from *Penicillium funiculosum*", Agricultureal and Biological Chemistry, 1985, pp. 2137-2146, vol. 49, No. 7.

* cited by examiner

*Primary Examiner*—Sreeni Padmanabhan
*Assistant Examiner*—Umamaheswari Ramachandran
(74) *Attorney, Agent, or Firm*—Wenderoth, Lind & Ponack, L.L.P.

(57) ABSTRACT

There is provided a plant disease resistance-inducing composition comprising a filamentous fungus-derived glycosphingolipid. There is also provided a method for controlling a plant disease, comprising the step of treating a target plant with a composition comprising a filamentous fungus-derived glycosphingolipid.

13 Claims, 1 Drawing Sheet

Results of Comparative Experiments
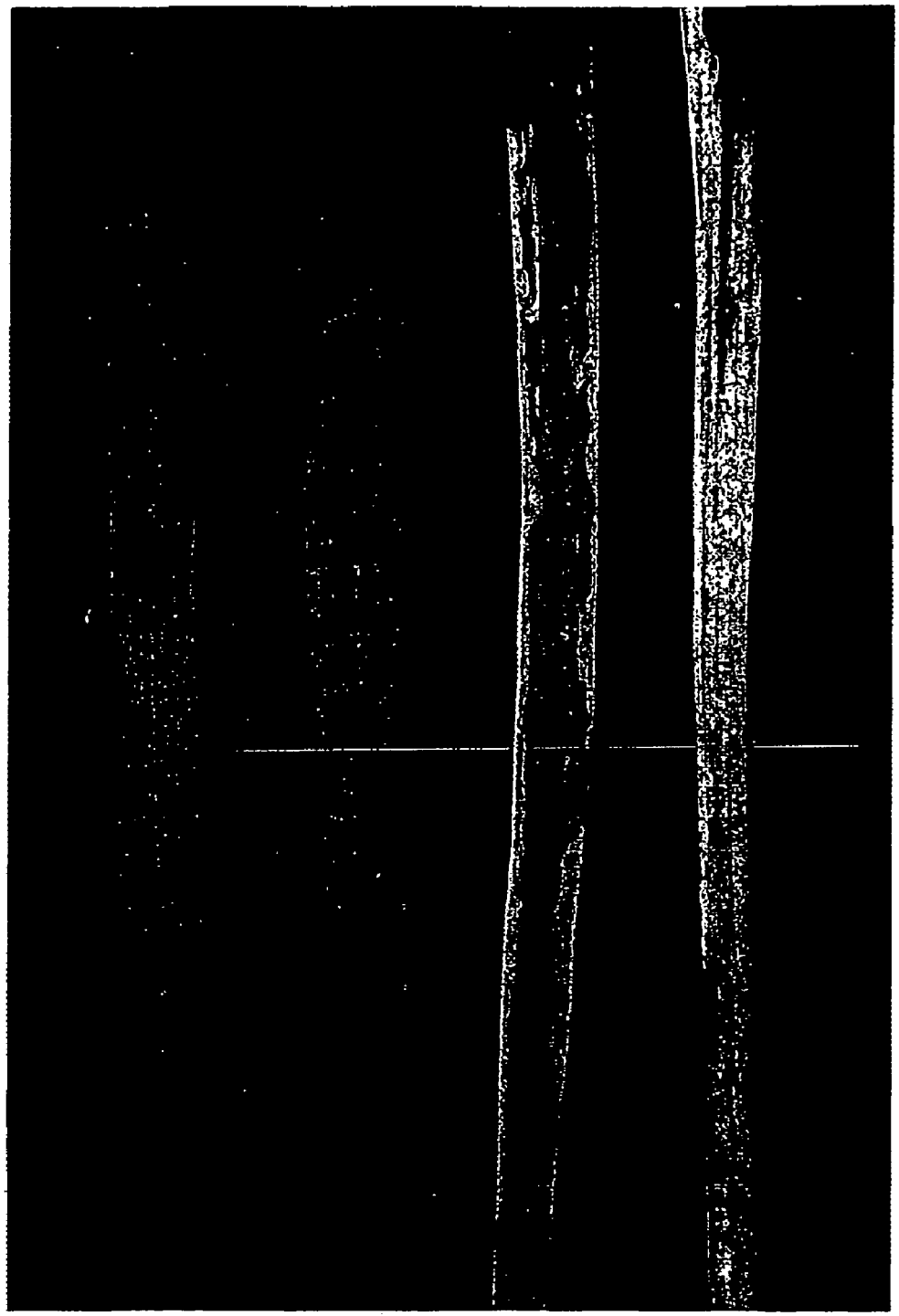
(1)　　　(2)　　(3)　　(4)
| The present invention (plot C1) | Extracts of the rice blast fungus (Plot C3) |

COMPOSITIONS INDUCING PLANTS DISEASE-RESISTANCE AND PROCESS FOR PRODUCING THE SAME

This application is a 371 of PCT/JP02/08686, filed Aug. 28, 2002, which claims priority to Japanese Application No. 2001-257800, filed Aug. 28, 2001, the entirety of which is hereby incorporated by reference.

BACKGROUND OF THE INVENTION

1. Field of the Invention

The present invention relates to a plant disease resistance-inducing composition, which uses mycelia or fruit bodies of filamentous fungi as a raw material, is environmentally friendly, and is safe to users and consumers, and a process for producing the composition.

2. Background Art

Major conventional disease control methods for agricultural products include a method in which a chemical pesticide such as a fungicide or an invasion inhibiting agent is used, and a method in which a microorganism pesticide such as antagonistic microorganisms or an organism such as a natural enemy organism is used.

In most of chemical pesticides, diseases are controlled by direct action on plant pathogenic fungi. In addition to the chemical pesticides, resistance induction-type pesticides are used in which diseases of crops are controlled by enhancing the disease resistance possessed by plants per se.

The pesticides in most cases exhibit definite action on the plant pathogenic fungi. Continuous use of these pesticides in many cases results in the appearance of mutants resistant to the pesticides. On the other hand, the resistance induction-type pesticides control disease infection by the induction of the resistance of plants rather than the action directly on the plant pathogenic fungi. By virtue of this mechanism, for the resistance induction-type pesticides, up to now, there is no report on the appearance of resistant mutants. Therefore, it is considered that the influence of the resistance induction-type pesticides on environment including other organisms is relatively small.

In agricultural production, the establishment of sustainable agricultural production techniques has been demanded. To meet this demand, the development of environment-conscious agricultural materials is an important task.

Further, an increasing consumer's demand for safer foods in recent years has led to an increase in an ever-increasing demand for organic agricultural products which have been cultivated by taking advantage of the natural cycling function of agriculture. According to the guideline published by The Ministry of Agriculture, Forestry and Fisheries of Japan, materials usable in the production of organic agricultural products are limited to naturally occurring useful mineral materials, plants, animals, and natural substances which have been removed, extracted, or prepared from them. When the use of them as pesticides, e.g., for the control of diseases and insect pests is desired, only pesticides registered based on the Agricultural Chemicals Regulation Law can be used, and antibiotics should not be used.

Thus, control materials usable in the production of organic agricultural products are limited. Therefore, naturally occurring substance-derived highly effective disease control agents as an alternative to the conventional chemical pesticides have been desired. The supply of agricultural materials, which have the above resistance induction-type disease control effects, that is, can prophylactically control diseases, and are derived from naturally occurring materials, could realize pesticides which are safe to agricultural producers as users and consumers and, at the same time, can reduce an environmental burden.

Up to now, pesticides intended for disease resistance induction of plants have been limited to "Oryzemate" (generic name: probenazole, manufactured by Meiji Seika Kaisha Co., Ltd.) and "Bion" (generic name: acibenzolar-S-methyl, manufactured by Novartis) which are registered as rice blast control agents.

Phytoalexin inducers such as decomposition products of polysaccharides (Japanese Patent Laid-Open Publication No. 331016/1993) and uasmonic acid derivatives (Japanese Patent Laid-Open Publication No. 29412/1999) are reported as other disease resistance-inducing substances.

In the above pesticides for disease resistance induction purposes, control effect against various crop diseases is provided by inducing the resistance of plants rather than the action directly on plant pathogenic fungi. Therefore, up to now, there is no report on the appearance of mutants resistant to these pesticides. All of them, however, are chemically synthesized pesticides and thus do not conform to the guideline. Further, it should be noted that, although the above phytoalexin inducers induce the production of phytoalexins which is a disease resistance reaction of plants, there is no clear description on practical disease control effect in the above publications.

Likewise, cerebrosides which have been reported as phytoalexin inducers are known as having control effect on a practically usable level against rice diseases (Japanese Patent No. 2846610 and WO 98/47364). Cerebrosides are a kind of glycosphingolipids and are glycolipids in which hexose is attached to primary alcohol of ceramide through glycoside linkage. Glycosphingolipids are universally present as constituents of membranes in various organism species and have already been used as highly safe cosmetic ingredients. Glycosphingolipids having disease resistance induction activity have been considered as being categorized as cerebrosides (Koga J. et al. (1998) J. Biol. Chem. 48 (27), 31985-31991). Cerebroside B is known to be distributed in *Penicillium funiculosum* (Kawai G., Ikeda Y., Tubaki K. (1985) Agric. Biol. Chem. 49 (7), 2137-2146), *Lentinus edodes* (Kawai G (1989) Biochim. Biophys. Acta 1001 (2) 185-190), *Pachybasium* sp. (Sitrin R. et al. (1988) J. Antibiot. 41 (4), 469-480), and *Rhizoctonia* sp. (Umemura K. et al. Plant Cell Physiology 41(6), 676-683). Cerebroside B has a structure represented by formula (I):

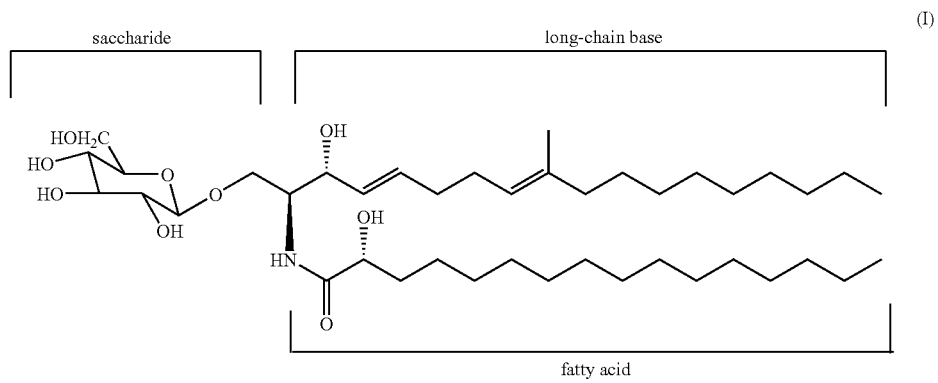

(I)

Cerebroside B is disclosed as a rice disease control agent in WO 98/47364. The control agent disclosed in this patent is one extracted from plant pathogenic fungi. Further, it should be noted that, up to now, there is no report on the disease control effect of cerebroside B and other cerebrosides against agricultural products other than rice.

Regarding the distribution of cerebrosides in Basidiomycetes, it is known that cerebrosides are contained in an ethanol extract of a fruit body of raw Shiitake mushroom (*Lentinus edodes*) (Kawai G (1989) Biochim. Biophys. Acta 1001(2) 185-190) and cerebrosides can be extracted with acetone from a cultured mycelium of *Schizophyllum commune* Fr. (Japanese Patent Publication No. 52878/1988). However, the activity of the substances described in the above publications is fruit body inducing activity, and control effect against diseases of plants is not described therein.

Regarding the utilization of extracts of Basidiomycetes in crop cultivation, for example, Japanese Patent Publication No. 44040/1981 describes the utilization of the extracts for increasing the yield of agricultural products or for growth promotion purposes, and Japanese Patent Publication No. 48087/1982 describes the utilization of the extracts for pigmentation promotion and sugar content enhancement in citrus. All of these actions, however, are exhibited by aqueous extracts.

In general, the activity of disease resistance-inducing substances is known to vary depending upon plant species. Glucans, which are polymers of glucose, are known as representative examples of microorganism-derived resistance-inducing substances which have hitherto been reported. Glucans which induce the disease resistance of soybeans do not induce any resistance reaction in rice plants. On the other hand, glucans, which induce the disease resistance of rice plants, do not have any resistance inducing capability in soybeans (Sharp K. (1984) J. Biol. Chem. 259, 11321-11336, and Yamaguchi T. (2000) Plant Cell 12, 817-826), indicating that, despites substances categorized as glucans, the reaction of crop species vary depending upon polymerization methods. Further, arachidonic acids are reported to induce resistance of potatoes (Bostock M. (1981) Science 212, 349-360). However, there is no report on the induction of resistance in crops other than potatoes. Thus, resistance-inducing substances are considered to have crop species-dependent specific activity.

SUMMARY OF THE INVENTION

Under these circumstances, the present inventors have made studies on a plant disease resistance-inducing composition which uses, as a raw material, a wide variety of filamentous fungi including edible fungi and comprises, as an active ingredient, a glycosphingolipid contained in filamentous fungi. As a result, they have surprisingly found that filamentous fungus-derived glycosphingolipids have control effect against diseases of rice plants, as well as against diseases of various crop species other than the rice plants.

Further, the present inventors have found that liposoluble substances, which have been extracted together with glycosphingolipids from filamentous fungi, can effectively act as a spreader. When glycosphingolipids are extracted from filamentous fungi and are used as an active ingredient, there is no need to newly add a spreader because liposoluble substances are also extracted together with the glycosphingolipids. This is very advantageous from the viewpoints of working efficiency and cost reduction. The present inventors have further found that a composition containing a liposoluble substance extracted from filamentous fungi has a high level of active ingredient penetration transfer to plants.

Furthermore, the present inventors have found that a crude extract provided by extraction with an organic solvent from glycosphingolipid-containing filamentous fungi has plant growth inhibitory activity. The present inventors have found that substances having physiologically inhibitory activity against plants are contained as an impurity of resistance-inducing substances in the crude extract of filamentous fungi with an organic solvent. The present inventors have succeeded in effectively removing the physiologically inhibitory substances in a concentration/separation step.

Accordingly, an object of the present invention is to provide a resistance induction-type disease control composition which uses, as a raw material, safe filamentous fungi having experience in ingestion or the like, does not have any physiologically inhibitory activity against plants, has a wide control spectrum with respect to various crop species, and is environmentally friendly.

According to one aspect of the present invention, there is provided a plant disease resistance-inducing composition comprising a filamentous fungus-derived glycosphingolipid.

According to another aspect of the present invention, there is provided a process for producing the composition according to the present invention, comprising the steps of: stirring mycelia or fruit bodies of a filamentous fungus dipped in an organic solvent to extract a glycosphingolipid and a liposoluble substance into the organic solvent (organic solvent extraction step); and concentrating the extract provided by the organic solvent extraction in the extraction step and then precipitating and removing substances, having physiologically inhibitory activity against plants, contained in the extract (concentration/separation step).

DETAILED DESCRIPTION OF THE INVENTION

The term "glycosphingolipid" as used herein refers to a compound comprising a long-chain base, a fatty acid, and a saccharide as represented by formula (I). In this context, the type of saccharide and the number of saccharides are not particularly limited.

The term "cerebrosides" as used herein refers to glycosphingolipids in which the saccharide part is hexose.

The structure of the filamentous fungus-derived glycosphingolipid is characterized by having a methyl group attached to the 9-position of the long-chain base part (Kawai G., Ikeda Y., Tubaki K. (1985) Agric. Biol. Chem. 49 (7), 2137-2146 and Kawai G (1989) Biochim. Biophys. Acta 1001 (2) 185-190). The structure is known to be involved in the rice disease resistance-inducing activity (Koga J. et al. (1998) J. Biol. Chem. 48 (27), 31985-31991, and Umemura K. et al. (2000) Plant Cell Physiol. 41 (6), 676-683). Therefore, in the present invention, the term "filamentous fungus-derived glycosphingolipid" refers to a glycosphingolipid in which a methyl group is attached to the 9-position of the long-chain base part. Further, in the present invention, the term "filamentous fungus-derived cerebrosides" refers to cerebrosides in which a methyl group is attached to the 9-position of the long-chain base part.

Filamentous fungus-derived cerebrosides include the following cerebrosides:

cerebroside A ((4E,8E)-N-D-2'-hydroxy-(E)-3'-hexadecenoyl-1-O-β-D-glucopyranosyl-9-methyl-4,8-sphingadienine);

cerebroside B ((4E,8E)-N-D-2'-hydroxypalmitoyl-1-O-β-D-glucopyranosyl-9-methyl-4,8-sphingadienine);

cerebroside C ((4E,8E)-N-D-2'-hydroxy-(E)-3'-octadecenoyl-1-O-β-D-glucopyranosyl-9-methyl-4,8-sphingadienine); and cerebroside D ((4E,8E)-N-D-2'-hydroxystearoyl-1-O-β-D-glucopyranosyl-9-methyl-4,8-sphingadienine).

The composition according to the present invention may comprise cerebroside A, cerebroside B, cerebroside C, and cerebroside D either solely or in a combination of two or more.

The glycosphingolipid contained as an active ingredient in the composition according to the present invention may be prepared from mycelia or fruit bodies of filamentous fungi.

Preferred filamentous fungi include microorganisms belonging to Basidiomycetes and microorganisms for fermentation production such as enzyme production, antibiotics production, and polysaccharides production.

Basidiomycetes include edible Basidiomycetes such as microorganisms belonging to genus *Pleurotus*, genus *Lentinus*, genus *Flammulina*, genus *Grifola*, genus *Agaricus*, genus *Auriculariales*, genus *Tremellales*, genus *Pholiota*, and genus *Sparassidaceae*, and medical Basidiomycetes such as microorganisms belonging to genus *Wolfiporis* or genus *Ganoderma*. Microorganisms for fermentation production include those belonging to genus *Aspergillus*, genus *Penicillium*, genus *Trichoderma*, genus *Acremonium*, genus *Mucor*, and genus *Rhizopus*. Examples of preferred Basidiomycetes usable herein include *Lentinus edodes*, *Pleurotus ostreatus*, *Flammulina velutipes*, *Glifola frondosa*, *Agaricus bisporus*, *Agaricus campestris*, and *Auricularia polytricha*. Examples of preferred microorganisms for fermentation production include *Aspergillus niger*, *Aspergillus oryzae*, and *Penicillium roquefortii*.

Mycelia or fruit bodies of filamentous fungi may be, for example, vial cells, culture solution of cells, concentrate of culture solution, dried cells, or processed product thereof including fermentation residue or the like. Preferred are dried cells of fruit bodies.

When dried cells of filamentous fungi are used, grinding of the dried cells by means of a grinding machine such as a power mill to such an extent that a solvent can easily infiltrate the dried cells can realize extraction with high efficiency. Fine grinding to such an extent that the particles are passed through a sieve having an opening of about 2 mm is preferred from the viewpoint of realizing extraction with higher efficiency.

In a preferred embodiment of the present invention, there is provided a process for producing a plant disease resistance-inducing composition, comprising the steps of: stirring mycelia or fruit bodies of a filamentous fungus dipped in an organic solvent to extract components contained in the cells into the organic solvent (organic solvent extraction step); and concentrating the extract provided by the organic solvent extraction in the extraction step and then precipitating and removing substances, having physiologically inhibitory activity against plants, contained in the extract (concentration/separation step). The composition thus obtained comprises a glycosphingolipid as an active ingredient and a liposoluble substance as a spreader component.

In the present invention, the term "liposoluble substance" refers to a substance which can be made soluble in fats and oils, and many of such liposoluble substances can be extracted with an organic solvent. The liposoluble substance can be simply quantitatively determined by extraction and determination using n-hexane. The liposoluble substance derived from mycelia or fruit bodies of filamentous fungi can be extracted from filamentous fungi simultaneously with the extraction of glycosphingolipids as the active ingredient. The extracted liposoluble substance contains an amphiphatic substance having spreading activity which, upon application of the composition, can improve the spreading of the composition on leaves. Therefore, the spreading and penetration transfer of the glycosphingolipid as the active ingredient on the plant body can be enhanced. In the plant disease resistance-inducing composition according to the present invention, when the active ingredient is extracted from filamentous fungi, the extract contains a spreader component. Therefore, the addition of any additional spreader at the time of application is not required. Even if the use of an additional spreader is required, the addition of only a small amount of the spreader suffices for contemplated results. This is advantageous from the viewpoints of working efficiency and cost reduction and, at the same time, can reduce an influence on the environment.

In the extraction step, an organic solvent is added to the filamentous fungus, the mixture is stirred, and, after the completion of the extraction of the active ingredient, and solid-liquid separation is carried out for separation into an organic solvent extract and the residue to provide the organic solvent extract. Organic solvents usable in the extraction step include ethanol, methanol, hexane, petroleum ether, ethyl ether, ethyl acetate, chloroform, and acetone. Solvents, which are preferred for achieving good extraction efficiency, include ethyl acetate and chloroform. When the composition is used as a disease control agent usable in the cultivation of organic agricultural products, however, the use of ethanol is preferred.

Proper extraction conditions are selected according to the organic solvent used and the state of the filamentous fungus. The liquid temperature in the extraction is preferably 15 to 80° C. Further, in order to improve the yield, the residue may be reextracted to further obtain the active ingredient. To this end, a method may be adopted wherein an organic solvent is again added to the residue after the solid-liquid separation to dip the residue in the organic solvent, and the mixture is subjected to solid-liquid separation to separate an organic solvent extract which is then added to the previously obtained organic solvent extract.

In the concentration/separation step, the organic solvent extract can be concentrated to enhance the content of the active ingredient and the spreader ingredient and, at the same time, to remove substances having physiologically inhibitory activity against plants.

The concentration can be carried out by a conventional method such as freeze drying, vacuum concentration, or heat distillation. Since, however, concentration at elevated temperatures is unfavorable, vacuum concentration is preferred. In the case of the heat distillation, the concentration is carried out at a temperature up to 80° C.

The concentration may be carried out so that, in the concentrate, the cerebroside B content is preferably 0.4 to 3.0 mg/ml, more preferably 0.9 to 3.0 mg/ml, and the liposoluble substance content in terms of n-hexane extract is preferably 10 to 200 mg/ml, more preferably 30 to 100 mg/ml. It is a matter of course that the concentration may be carried out using, as an index, the content of a cerebroside other than cerebroside B. In the concentration, the volume is preferably reduced to one-fifth to one-thirtieth, more preferably one-tenth to one-twentieth of the volume before the concentration.

In the concentrate, when the liposoluble substance content in terms of an n-hexane extract is less than 10 mg/ml, the component having physiologically inhibitory activity against plants cannot be sometimes removed as precipitate. On the other hand, excessive concentration to a liposoluble substance content of more than 200 mg/ml sometimes causes the separation of the liposoluble substrate upon dilution which makes it impossible to provide a homogeneous component.

The formulation of the plant disease resistance-inducing composition according to the present invention may be any one adopted in pesticides, and examples thereof include liquid formulations, dust, granules, emulsifiable concentrates, wettable powder, oil solutions, aerosols, and floables. The form of the chemical for application, application form, and application method are also not particularly limited. The concentration of the composition at the time of application is, however, preferably 0.5 to 100 μg/ml, more preferably 1 to 50 μg/ml, particularly preferably 5 to 20 μg/ml, in terms of the content of cerebrosides. The application concentration, however, may be regulated to a proper value depending upon the type of plants, growth stage, and application method.

The plant disease resistance-inducing composition according to the present invention may be used for the protection of all cultivation plants, and examples of such cultivation plants include cereals (for example, rice, barley, wheat, and corn), Solanaceae plants (for example, tomatoes, eggplant, and potatoes), Cucurbitaceae plants (for example, cucumbers, melons, and pumpkins), Leguminous plants (for example, peas and soybeans), Cruciferous plants (for example, Japanese radishes, Chinese cabbages, and cabbages), Rosaceae plants (for example, strawberries, apples, and pears), Compositae plants (for example, lettuces), Convolvulaceae plants (for example, sweet potatoes), Umbelliferae plants (for example, carrots, parsley, and celery), and Vitaceae plants (for example, grapevines). In plants, a general disease resistance reaction is considered to be nonspecific to pathogenic fungi. Therefore, all plant diseases induced by filamentous fungi may be mentioned as target diseases of the above crops, and examples thereof include rice blast fungus (*Magnaporthe grisea*), rice southern leaf blight fungus (*Cochliobolus miyabeanus*), sweet potato dead arm fungus (*Fusarium oxysporum*), melon dead arm fungus (*Fusarium oxysporum* f. sp. *melonis*), lettuce root rot fungus (*Fusarium oxysporum* f. sp. *lactucae*), and tomato verticullium wilt fungus (*Verticillium dahliae*).

In a preferred embodiment of the present invention, there is provided a plant disease resistance-inducing composition comprising filamentous fungus-derived glycosphingolipid and liposoluble substance, the glycosphingolipid comprising cerebroside B.

Further, in a preferred embodiment of the present invention, there is provided a plant disease resistance-inducing composition comprising filamentous fungus-derived glycosphingolipid and liposoluble substance, the glycosphingolipid comprising cerebroside B, the content of cerebroside B being 0.4 to 3.0 mg/ml, the content of the liposoluble substance being 10 to 200 mg/ml in terms of an n-hexane extract.

In another embodiment of the present invention, there is provided a method for inducing disease resistance in a target plant, comprising the step of treating the target plant with a composition comprising a filamentous fungus-derived glycosphingolipid.

Further, in a further embodiment of the present invention, there is provided a method for controlling a plant disease, comprising the step of treating the target plant with a composition comprising a filamentous fungus-derived glycosphingolipid.

EXAMPLES

The present invention is further illustrated by the following examples that are not intended as a limitation of the invention.

Example 1

Production of Plant Disease Resistance-inducing Composition (1) Organic Solvent Extraction Step A dried shiitake mushroom (*Lentinus edodes*) was ground in a power mill (table power mill P-02, manufactured by SHOWA GIKEN INDUSTRIAL CO., LTD.), and a ground product was collected through a screen having an opening size of 1.0 mm. To 1 kg of the ground product of the dried shiitake mushroom was added 5 liters of 99.5% ethanol. The mixture was kept at 25° C., and extraction was carried out for 24 hr with stirring, followed by solid-liquid separation into a first ethanol extract and the residue. Further, the residue was dipped in 5 liters of 99.5% ethanol for 30 min to wash the residue, followed by separation into a second ethanol extract and the residue. The first and second ethanol extracts were combined together to provide an ethanol extract.

(2) Concentration/separation Step

The combined ethanol extract provided in the organic solvent extraction step was concentrated under atmospheric pressure at a liquid temperature of 80° C. until the volume of the liquid became about one-twentieth of the initial volume. After the concentration, the concentrate was cooled to room temperature, and the resultant precipitate in the liquid was removed by centrifugation to give about 80 ml of ethanol extract concentrate A. The content of liposoluble substances in the ethanol extract concentrate A was determined by an n-hexane method, and the content of cerebroside B in the ethanol extract concentrate A was determined by an HPLC method. As a result, the liposoluble substance content and the cerebroside B content were found to be 100 mg/ml and 2.2 mg/ml, respectively.

(3) Analysis of Extract

The extract obtained above was analyzed as follows.

enizer AM-7, manufactured by Nihon Seiki Seisakusho Co., Ltd). The attrited liquid was transferred to a centrifugal sedimentation tube and was then shaken on a shaker (a spinning reciprocal shaker R-30, manufactured by TIETECH Co., Ltd.) for 12 hr to extract cerebrosides into the organic solvent layer. The amounts of solvent-extracted cerebrosides were measured by the above HPLC and were expressed in terms of the amounts of cerebroside B and cerebroside D per g of the raw shiitake mushroom. The results are shown in Table 1. It was found that several kinds of cerebrosides other than cerebroside B and cerebroside D were contained in the extract (data omitted). These cerebrosides corresponded to Kawai et al. (Biochimica et Biophysica Acta, 1001, 1989, 185-190) Len I to X.

TABLE 1

|  | Methanol extraction | Ethanol extraction | Chloroform extraction | Acetone extraction | n-hexane extraction | Ethyl acetate extraction |
| --- | --- | --- | --- | --- | --- | --- |
| Cerebroside B content, µg/g | 25.6 | 28.8 | 35.6 | 25.8 | 27.8 | 50.4 |
| Cerebroside D content, µg/g | 0.3 | 0.3 | 0.4 | 0.3 | 0.3 | 0.6 |

The extract was analyzed by HPLC using a TSKgel ODS 120A (manufactured by Tosoh Corporation; 4.6 mm×300 mm) column to determine cerebroside B content and cerebroside D content. In the analysis, under conditions of column temperature 50° C., 80% ethanol solvent, and flow rate of 1 ml/min, the amounts of substances detected by UV at 215 nm in retention times of 20.8 min and 24.6 min were quantitatively determined respectively as cerebroside B content and cerebroside D content.

The liposoluble substance content was determined as an n-hexane extract (according to a table appended to Notification No. 28 of the Environmental Agency of Japan in 1985). Specifically, 50 ml of deionized water was placed in a 100-ml separatory funnel, and 1 ml of a sample solution was added to the deionized water. Subsequently, 10 ml of n-hexane and 0.5 g of NaCl were added thereto, and the mixture was shaken and allowed to stand. After separation, the lower layer was removed, and 50 ml of water was added again for washing with water. This washing with water was repeated twice, and the hexane layer was recovered. A satisfactory amount of anhydrous sodium sulfate was added to the hexane layer for dehydration. The mixture was then filtered through No. 2 filter paper (trademark; ADVANTEC, manufactured by Toyo Roshi Kaisha, Ltd.), and the filter paper was washed with a minor amount of hexane. The extract was transferred to an evaporation container and was evaporated on a hot plate of 80° C., followed by drying in a dryer (80° C.). The dried product was weighed as an n-hexane extract.

Example 2

For comparison of the cerebroside extraction rate between different organic solvents, the amounts of cerebroside B and cerebroside D extracted from a raw shiitake mushroom were measured to determine the cerebroside B and cerebroside D contents of the extract. Methanol, ethanol, chloroform, acetone, n-hexane, and ethyl acetate were used as comparison organic solvents. Each solvent (150 ml) and 30 ml of water were added to 100 g of the raw shiitake mushroom which was then attrited in a watering blender (Ace Homog- Example 3

Relationship Between Cerebroside B Content, Lipid Content, and Concentration Ratio and Protective Value for Rice Blast Concentrates with respective concentrations provided in the course of the preparation of ethanol extract concentrate A in Example 1, and a solution obtained by further concentrating extract concentrate A were examined for the liposoluble substance content, the cerebroside B content, and the control effect for rice blast. For the concentrations of the individual concentrates, the ethanol extract after the completion of the extraction step was regarded as a one-fold diluted solution, and the ratio of the amount of the liquid after the completion of the extraction to the amount of the liquid after each concentration operation in the concentration/separation step was regarded as the concentration ratio. In this way, 1-, 2-, 5-, 10-, 20-, 30-, and 50-fold diluted solutions were provided for the test. The liposoluble substance content was expressed in terms of an n-hexane extract. Further, for the individual liquids, the spreadability of the testing liquids, state of the liquids upon dilution, the state of the foliar surface as the level of physiological disorder of the liquid applied leaves were compared.

To examine the disease control effect, an evaluation test was carried out by the following method. Specifically, 8 forcibly germinated rice seeds (variety: Akitakomachi) per pot were sowed and were raised in an air-conditioned room, and the sample was sprayed on the plant with 3- to 4-foliar age stage in true leaves. In this case, five pots were provided per plot, and the plant was treated with a liquid prepared by diluting a solution with each concentration ratio to 10 ppm in terms of cerebroside B. For the comparison test, the plant was treated with a liquid prepared by diluting a standard sample of cerebroside B to 10 ppm. The test liquid (2 ml per pot) was applied to the foliage, and the plant was allowed to stand for one hr until the test liquid on the foliage was brought to a dried state and was then raised again in the air-conditioned room. The standard sample of cerebroside B was a standard sample (2 mg/ml cerebroside B solution)

(Plant Cell Physiology 41 (6), 676-683 (2000)) separated and purified by the method of Umemura et al.

Three days after the sample treatment, infection treatment was carried out by spray inoculation of a conidial suspension of rice blast fungus (*Magnaporthe grisea*, race: 007). After the spray inoculation, the plant was allowed to stand under dark and humidified conditions for 36 hr to infect the plant with the rice blast fungus. Thereafter, the plant was transferred to the air-conditioned room for raising. Five days after the inoculation, the number of diseased lesions produced in the third true leaf in each plot was counted to calculate the protective value. The protective value was calculated by the following equation: protective value=(1−average number of lesions per leaf in treatment plot/average number of lesions per leaf in control plot)×100. For the control plot, water in an amount of 2 ml per pot was sprayed.

The results are summarized in Table 2. When the samples with low concentration ratios were used, the foliage was discolored, indicating that the plant was disordered. On the other hand, when the samples with high concentration ratios were used, the diluted liquids are subjected to separation which deteriorated the protective value and the operability. From a comprehensive perspective of the state of the folia, the spreadability, the state of the liquid upon dilution, and the protective value, it is considered that the extract is preferably concentrated to give a cerebroside B concentration of 0.4 to 3.0 mg/ml and a liposoluble substance content of 10 to 200 mg/ml in terms of an n-hexane extract.

was 2.3; and, for ethanol extract concentrate A treatment plot (A), the average number of lesions per leaf was 1.8, indicating that, in all the plots, significant disease development inhibitory effect was observed. For the protective value, ethanol extract concentrate A treatment plot (A) according to the present invention was higher than cerebroside B (with spreader Tween 20 added thereto) treatment plot (B).

TABLE 3

|  | Experimental plot A | Comparative plot B | Control plot |
|---|---|---|---|
| Number of lesions | 1.8 | 2.3 | 18.6 |
| Protective value | 90.3 | 87.6 | 0 |

Example 5

Rice Brown Spot Control Test (1) Method

In the same manner (raising of test plant, sample treatment method and treatment concentration, and pathogenic

TABLE 2

| Concentration ratio | 1 (just after extraction) | 2 | 5 | 10 | 20 (extract A) | 30 | 50 | Standard sample of cerebroside B |
|---|---|---|---|---|---|---|---|---|
| Cerebroside B content, mg/ml | 0.09 | 0.18 | 0.45 | 0.89 | 1.87 | 2.89 | 4.96 | — |
| Liposoluble substance, mg/ml | 3 | 7 | 14 | 32 | 68 | 98 | 219 | — |
| Protective value | 80 | 85 | 88 | 91 | 92 | 93 | 70 | 90 |
| Spreadability | ○ | ○ | ○ | ○ | ○ | ○ | ○ | X |
| State of foliar surface | X | X | Δ | ○ | ○ | ○ | ○ | ○ |
| State of liquid upon dilution | ○ | ○ | ○ | ○ | ○ | Δ | X | ○ |

Spreadability: ○ normal, X water-repellent.
State of foliar surface: ○ normal, X yellowed or discolored due to disorder, Δ partially discolored.
State of liquid upon dilution: ○ normal, X oil separated, Δ partially separated.

Example 4

Rice Blast Control Test (1) Method

The control effect was evaluated in the same manner as in Example 3. Ethanol extract concentrate A prepared in Example 1 was diluted with water to give a 300-fold diluted liquid (10 ppm in terms of cerebroside B), and the test liquid in an amount of 2 ml per pot was applied to the foliage of test liquid treatment plot (A). On the other and, 0.1% of Tween 20 as a spreader was added to a 10 ppm solution of cerebroside B to give a test liquid. This test liquid was applied in an amount of 2 ml per pot to the foliage in test liquid treatment plot (B).

(2) Results

The results are shown in Table 3. For the control plot, the average number of lesions per leaf was 18.6; for cerebroside B treatment plot (B), the average number of lesions per leaf fungus infection method) as in the rice blast control test in Example 3, control effect against rice Brown spots in ethanol extract concentrate A treatment plot (A) and cerebroside B treatment plot (B) was examined. The counting of the number of lesions was carried out two days after the spray inoculation of a conidial suspension of Brown spot fungus (*Cochliobolus miyabeanus*).

(2) Results

The results are shown in Table 4. For the control plot, the average number of lesions per leaf was 10.2; for cerebroside B treatment plot (B), the average number of lesions per leaf was 1.3; and, for ethanol extract concentrate A treatment plot (A), the average number of lesions per leaf was 0.9, indicating that significant disease development inhibitory effect was observed. For the inhibitory effect, ethanol extract concentrate A treatment plot was better than cerebroside B treatment plot.

TABLE 4

|  | Experimental plot A | Comparative plot B | Control plot |
|---|---|---|---|
| Number of lesions | 0.9 | 1.3 | 10.2 |
| Protective value | 91.1 | 87.3 | 0 |

Example 6

Field Test for Rice Blast Control (1) Method

A rice cultivation field in a region where blast usually takes place was randomly divided into test plots (each 24 m$^2$). On the 44th and 51st days after the transplantation of seedling rice (variety: Koshihikari), test liquid application treatment was carried out. Spray treatment was carried out in 120 L/10 are for each 3 blocks per plot. Samples in individual plots were as follows. Experimental plot (E) was treated with a liquid (concentration: 20 ppm in terms of cerebroside B) prepared by diluting ethanol extract concentrate A prepared in Example 1 with water by 150 times. Comparison plot (F) was treated with a cerebroside B solution having a cerebroside B concentration of 20 ppm and containing, added thereto, about 0.02 to 0.03% of Mylinow (Mairinou) (manufactured by Nihon Nohyaku Co., Ltd.) as a spreader. Comparison plot (G) was treated with a liquid prepared by adding about 0.02 to 0.03% of Mylinow (manufactured by Nihon Nohyaku Co., Ltd.) as a spreader to a 1000-fold diluted liquid of Rabcide Flowable (manufactured by Kureha Chemical Industry Co., Ltd.) (active ingredient: 500 ppm of fthalide).

(2) Results

One month after the initial application, the plants were investigated for leaf blast development, and the comparison of the plots was done in terms of protective value determined from the percentage disease development. The results are shown in Table 5. The protective value was 95 for ethanol extract concentrate A treatment plot (E), 93 for cerebroside B treatment plot (F), and 94 for comparison plot (G), indicating that these samples are effective for rice blast control. Further, the protective value in ethanol extract concentrate A treatment plot (E) was higher than that in cerebroside B treatment plot (F). Thus, it could be confirmed that, in an actual cultivation field, the effect attained by the plant disease resistance-inducing composition according to the present invention usable in the cultivation of organic agricultural products is equal to or superior to that attained by agricultural chemicals.

TABLE 5

|  | Experimental plot E | Comparison plot F | Comparison plot G | Control plot |
|---|---|---|---|---|
| Protective value | 95 | 93 | 94 | 0 |

Example 7

Sweet Potato Stem Rot Control Test (1) Method

The root parts of seedling sweet potatoes (variety: Benikomachi) infected with sweet potato dead arm fungus (Fusarium oxysporum) were submerged in each sample solution for 30 min before planting in a field. Individual plots were treated by the following sample liquids. Experimental plot (E) was treated with a liquid (concentration: 20 ppm in terms of cerebroside B) prepared by diluting ethanol extract concentrate A prepared in Example 1 by 150 times. Comparison plot (H) was treated with a liquid having a cerebroside B concentration of 20 ppm. The number of plants per plot was 20, and one plot consisted of four blocks which were provided at intervals of 60 cm. In this state, the plants were transplanted in the field.

(2) Results

The percentage disease development of roots was investigated 26 days after the transplantation, and the protective value was calculated from the average percentage disease development of roots. The results are shown in Table 6. The protective value was 79 for ethanol extract concentrate A treatment plot (E) and 70 for cerebroside B treatment plot (H). Thus, it could be confirmed that the disease resistance-inducing composition according to the present invention also has control effect against solid disease. Since there is little or no fungicide effective for the soil disease, the control of the soil disease is said to be difficult. For this reason, soil fumigants are generally used. Because of its limited effect and from the viewpoint of environmental pollution, however, the development of an alternative technique has been desired. It has been found that the use of the disease resistance-inducing composition according to the present invention can be one of solid disease control methods utilizing the resistance-inducing action of crops.

TABLE 6

|  | Experimental plot E | Comparative plot H | Control plot |
|---|---|---|---|
| Protective value | 79 | 70 | 0 |

Example 8

Melon Fusarium Wilt Control Test (1) Method

Melon plants (variety: Ams) (third- or fourth-leaf (true leaf) developed) were submerged in each test liquid for 10 hr. Thereafter, conidia of melon dead arm fungus (*Fusarium oxysporum* f. sp. *melonis* race 2) cultured in a potato-dextrose medium were inoculated by drenching. Experimental plot (E) was treated with a liquid (concentration: 20 ppm in terms of cerebroside B) prepared by diluting ethanol extract concentrate A prepared in Example 1 by 150 times. Comparison plot (H) was treated with a liquid having a cerebroside B concentration of 20 ppm.

(2) Results

The percentage disease development of roots was investigated 21 days after the inoculation, and the protective value was calculated from the average percentage disease development of roots. The results are shown in Table 7. The protective value was 63 for ethanol extract concentrate A treatment plot (E) and 52 for cerebroside B treatment plot (H). Thus, it could be confirmed that the disease resistance-inducing composition according to the present invention is very effective for the control of diseases in vegetables. This effect is considered attributable to the fact that the penetration transfer of the cerebroside as the active ingredient into the plant body can be enhanced by the spreading effect of the liposoluble substance contained in the disease resistance-inducing composition of the present invention upon application.

It is considered that this is attained by enhancing the spreading effect of the liposoluble substance contained in the disease resistance-inducing composition of the present invention upon the application and the penetration transfer of the cerebroside as the active ingredient into the plant body.

While there is no intention of being bound by the following theory, it is believed that, although the structure of the cerebroside is unstable in an aqueous solution, the cerebroside, together with the liposoluble substance contained in the composition of the present invention, forms a stable higher order structure which is relatively stable also in the plant body and is gradually transferred and diffused into the plant body. This penetration leads to expectation of more stable control effect and longer residual effect by virtue of low susceptibility to flow-out from the surface of leaves by rain, less susceptibility to photodegradation by sunlight, and no siginificant dependency of control effect upon the amount of the chemical liquid to be applied.

TABLE 7

|  | Experimental plot E | Comparative plot H | Control plot |
|---|---|---|---|
| Protective value | 63 | 52 | 0 | of 10 times (w/v) the raw mycelia weight. The solvent extract was subjected to the concentration/separation step as in Example 1 to reduce the volume of the extract to one-tenth of the original volume. Thus, physiologically inhibitory substances were separated, and plant disease resistance-inducing substances were concentrated to prepare a plant disease resistance-inducing composition.

The content of cerebroside B in the composition was measured by the above HPLC method to calculate the cerebroside B content per weight of the raw material. Further, each of the solvent extracts thus obtained was diluted with water to a concentration of 100 ppm in terms of cerebroside B, and the diluted solutions were then applied to the blades of rice plants. The elicitor activity 7 days after the application of the diluted solutions was measured using, as an index, the amount of phytoalexins induced in the leaf structure by the method described in WO 98/47364. The results are shown in Table 8. The amount of phytoalexins was expressed in terms of the total amount of phytocassanes A, B, C, and D and momilactones A and B.

As is apparent from the results, cerebroside B can be efficiently extracted particularly from Basidiomycetes. Further, it could be confirmed that the compositions prepared by extraction from individual filamentous fungi have a phytoalexin-inducing capability.

TABLE 8

|  | Shiitake mushroom | Hen of the wood | Oyster mushroom | *A. niger* | *P. roquefortii* | *M. prainii* | *R. delemar* |
|---|---|---|---|---|---|---|---|
| Cerebroside B content of composition, mg/ml | 2.75 | 2.48 | 2.38 | 0.48 | 0.49 | 0.52 | 0.51 |
| Cerebroside B content of reduced volume product, mg/g-weight | 0.23 | 0.21 | 0.20 | 0.04 | 0.04 | 0.05 | 0.05 |
| Induced phytoalexin content, mg/g-raw leaf | 8.6 | 8.5 | 8.4 | 8.3 | 8.4 | 8.2 | 8.4 |
| Liposoluble substance content, mg/ml | 100 | 98 | 95 | 28 | 30 | 33 | 32 |

Example 9

Freeze-dried fruit body of each of Shiitake mushroom (*Lentinus edodes*), hen of the wood (*Glifola frondosa*), and oyster mushroom (*Pleurotus ostreatus*) was extracted with ethyl acetate as a solvent. Separately, fungi belonging to the genus *Aspergillus* (*Aspergillus niger*), fungi belonging to the genus *Penicillium* (*Penicillium roquefortii*), fungi belonging to the genus *Mucor* (*Mucor prainii*), and fungi belonging to the genus *Rhizopus* (*Rhizopus delemar*) were cultured in a liquid medium containing 1% cornstarch, 1% molasses, and 1% corn steep liquor (pH 5.5 adjusted by the addition of an aqueous potassium hydroxide solution). The culture was centrifuged at 6,000×g for 20 min to collect mycelia, followed by solvent extraction with ethyl acetate in an amount Example 10

Lettuce Root Rot Control Test (1) Method

Lettuce (variety: Patriot) plants (third-leaf (true leaf) developed) were chemically treated 12 hr before inoculation and were then transplanted to soil contaminated with lettuce root rot fungus (*Fusarium oxysporum* f. sp. *lactucae* race SB1-1) (cell density: $3 \times 10^4$ CFU/g as measured by a dilution plate method) for infection inoculation. Experimental plots were treated with a solution (E) prepared by diluting ethanol extract concentrate A prepared in Example 1 with by 300 times (concentration: 10 ppm in terms of cerebroside B) by submersion treatment, application treatment, and watering treatment, and were treated with a 20 ppm cerebroside B solution (H) by submersion treatment. The effects attained by these treatments were compared.

(2) Results

On the 28th day after the transplantation, the disease development was investigated by utilizing internal symptoms. The degree of disease development was judged in terms of an index based on disease development level. The disease development level was evaluated according to the following criteria. 0: no fibrovascular bundle discolored; 1: less than one-third of fibrovascular bundle discolored; 2: one-third to two-third of fibrovascular bundle discolored; and 3: not less than two-third of fibrovascular bundle discolored. The protective value was calculated by equation: protective value=(average degree of disease development of control plot−average degree of disease development of experimental plot)/(average degree of disease development of control plot)×100. The results are shown in Table 9. The weight of the ground part as a product (a farm product) was also measured. As a result, in the case of the ethanol extract concentrate treatment (E), the protective value was 100 for the submersion treatment plot, 72 for the application treatment plot, and was 86 for the watering treatment plot. For the ground part of the raw lettuce, when the weight in the control plot was presumed to be 100, the weight was 693 for the submersion treatment plot, was 266 for the application treatment plot, and was 559 for the watering treatment plot. Thus, it could be confirmed that the disease resistance-inducing composition according to the present invention can exhibit control effect without limitation on any treatment method although optimal treatment conditions vary depending upon the type of crops and the target disease.

healthy leaves; 1: external symptom observed in leaf located in the lowest or second lowest position; 2: external symptom observed in substantially the half of the leaves; 3: external symptom observed in most of the leaves and fall of leaves also observed; and 4: roots blighted. The protective value was calculated by equation: protective value=(average degree of disease development of control plot−average degree of disease development of experimental plot)/(average degree of disease development of control plot)×100. The results are shown in Table 10. As is apparent from Table 10, in the case of the treatment (E) with the ethanol extract concentrate, when the treatment time was 3 hr, the protective value was 12, that is, the control effect was unsatisfactory. On the other hand, when the treatment time was 6 hr or longer, the protective value was about 60, indicating that, as compared with the comparison plot, distinct disease control activity was exhibited. The reason why the effect varies depending upon the treatment time is believed to be reside in that, since the control effect of the disease control composition according to the present invention is one provided by resistance induction, a certain time period is required for establishing the resistance on the plant side. Further, the fact that the protective value in the plot (H), which had been treated with the 20 ppm cerebroside B solution for 12 hr, was 60 shows that the liposoluble substance contained in the disease control composition according to the present invention can enhance the disease control activity of cerebroside independently of species of plants.

TABLE 9

| | Submersion treatment (E) | Application treatment (E) | Watering treatment (E) | Submersion treatment (H) | Control plot |
|---|---|---|---|---|---|
| Protective value | 100 | 72 | 86 | 78 | 0 |
| Raw weight ratio on ground part | 693 | 266 | 559 | 231 | 100 |

Example 11

Tomato Verticillium Wilt Control Test (1) Method

Tomato plants (variety: Hausumomotaro) (second-leaf (true leaf) expanded) were submerged in a solution (E) prepared by diluting ethanol extract concentrate A prepared in Example 1 by 150 times. After the submersion treatment, the tomato plants were transplanted to soil contaminated with tomato verticullium wilt fungus (*Verticillium dahliae*) (cell density: $5 \times 10^4$ CFU/g) for infection inoculation. Experimental plot E was treated with a solution prepared by diluting ethanol extract concentrate A by 150 times (concentration: 20 ppm in terms of cerebroside B) for 3, 6, 12, and 24 hr. Experimental plot H was treated with a 20 ppm cerebroside B solution for 12 hr. The control effects attained by these treatments were determined and compared.

(2) Results

On the 21st day after the transplantation, the control effect was examined by investigation into disease development in terms of an index based on the external symptom. The degree of disease development based on the external symptom was evaluated according to the following criteria. 0:

TABLE 10

| | 3 hr (E) | 6 hr (E) | 12 hr (E) | 24 hr (E) | 12 hr (H) | Control plot |
|---|---|---|---|---|---|---|
| Protective value | 12 | 56 | 68 | 64 | 60 | 0 |

The invention claimed is:

1. A plant disease resistance-inducing composition comprising a filamentous fungus-derived glycosphingolipid and a filamentous fungus-derived liposoluble substance, wherein said filamentous fungus is a microorganism belonging to edible Basidiomycetes selected from the group consisting of genus *Pleurotus*, genus *Flammulina*, genus *Grifola*, genus *Agaricus*, genus *Auricularia*, genus *Tremellales*, genus *Pholiota*, and genus *Sparassidaceae* or medical Basidiomycetes selected from the group consisting of genus *Wolfiporis* or genus *Ganoderma* or a microorganism for fermentation production selected from the group consisting of genus *Aspergilus*, genus, *Penicillium*, genus *Trichoderma*, genus *Acremonium*, genus *Mucor*, and genus *Rhizopus* wherein said glycosphingolipid cerebroside B ((4E,8E)-N-D-2'-hydroxypalmitoyl-1-O-β-D-glucopyranosyl-9-methyl-4,8- sphingadienine), wherein the content of cerebroside B ((4E,8E)-N-D-2'-hydroxypalmitoyl-1-O-β-D-glucopyranosyl-9-methyl-4,8-sphingadienine) is 0.4 to 3.0 mg/ml and the content of the liposoluble substance is 10 to 200 mg/ml in terms of an n-hexane extract.

2. The composition according to claim 1, wherein said glycosphingolipid is obtainable by extraction with an organic solvent from filamentous fungus.

3. The composition according to claim 2, wherein said glycosphingolipid is obtainable by concentrating the extract obtained by the extraction with the organic solvent from the filamentous fungus and then precipitating and removing substances having physiologically inhibitory activity against plants.

4. The composition according to claim 1, wherein said liposoluble substance is obtainable by extraction with an organic solvent from filamentous fungus.

5. The composition according to claim 1, wherein said liposoluble substance is obtainable by concentrating the extract obtained by the extraction with the organic solvent from the filamentous fungus and then precipitating and removing substances having physiologically inhibitory activity against plants.

6. The composition according to claim 1, wherein the content of cerebroside B ((4E,8E)-N-D-2'-hydroxypalmitoyl-1-O-β-D-glucopyranosyl-9-methyl-4,8-sphingadienine) is 0.9 to 3.0 mg/mi and the content of the liposoluble substance is 30 to 100 mg/ml in terms of an n-hexane extract.

7. The composition according to claim 1, wherein said microorganism for fermentation production is one for the production of enzyme, the production of antibiotics, and the production of saccharides.

8. The composition according to claim 1, wherein said microorganism belonging to the Basidiomycetes is selected from the group consisting of, *Pleurotus ostreatus, Flammulina velutipes, Glifola frondosa, Agaricus bisporus, Agaricus campestris*, and *Auricularia polytricha*.

9. The composition according to claim 1, wherein said microorganism for fermentation production is selected from the group consisting of *Aspergillus niger, Aspergillus oryzae, Penicillium roquefortii, Mucor prainii*, and *Rhizopus delemar*.

10. A method for controlling a plant disease, comprising the step of treating a target plant with the composition according to claim 1.

11. A process for producing the composition according to claim 1, comprising the steps of:

stirring mycelia or fruit bodies of a filamentous fungus dipped in an organic solvent to extract a glycosphingolipid and a liposoluble substance into the organic solvent (organic solvent extraction step); and concentrating the extract provided by the organic solvent extraction in the extraction step and then precipitating and removing substances, having physiologically inhibitory activity against plants, contained in the extract (concentration/separation step), wherein said glycosphingolipid comprises cerebroside B ((4E,8E)-N-D-2'-hydroxypalmitoyl-1-O-β-D-glucopyranosyl-9-methyl-4,8-sphingadienine), wherein the extract obtained by the organic solvent extraction is concentrated to give a concentrate having a cerebroside B ((4E,8E)-N-D-2'-hydroxypalmitoyl-1-O-β-D-glucopyranosyl-9-methyl-4,8-sphingadienine) content of 0.4 to 3.0 mg/ml and the content of the liposoluble substance content of 10 to 200 mg/ml in terms of an n-hexane extract.

12. The process according to claim 11, wherein the extract obtained by the organic solvent extraction is concentrated to give a concentrate having a cerebroside B ((4E,8E)-N-D-2'-hydroxypalmitoyl-1-O-β-D-glucopyranosyl-9-methyl-4,8-sphingadienine) content of 0.9 to 3.0 mg/ml.

13. The process according to claim 11, wherein the extract obtained by the organic solvent extraction is concentrated to give a concentrate having a liposoluble substance content of 30 to 100 mg/ml in terms of an n-hexane extract.

* * * * *